United States Patent [19]

Jacobs

[11] Patent Number: Plant 7,375

[45] Date of Patent: Nov. 6, 1990

[54] ROSE PLANT 'FOUTELL'

[76] Inventor: Betty A. Jacobs, 525 Butler Rd., Bakersfield, Calif. 93304

[21] Appl. No.: 354,282

[22] Filed: May 19, 1989

[51] Int. Cl.[5] ..... A01H 5/00

[52] U.S. Cl. ..... Plt./7

[58] Field of Search ..... Plt. 7, 10, 12

*Primary Examiner*—Howard J. Locker

[57] ABSTRACT

The subject of the present disclosure is a new and distinct variety of miniature rose plant characterized by bright orange-red buds and flowers with lighter near-white reverse on petals and of good substance and keeping qualities.

1 Drawing Sheet

1

The present invention relates to a new and distinct variety of hardy, dwarf, bush type rose plant of the miniature class: the variety being primarily characterized — as to novelty — by bright orange-red buds and flowers with lighter near-white reverse, and the general color effect being bright orange-red.

The variety is futher characterized by:

An abundance of bloom, with flowers, on mature plant, borne both singly and several together in loose spray or cluster.

Light fragrance.

A plant which is vigorous, of rounded, somewhat upright shape with semi-glossy, medium-small foliage with pointed leaflets; the buds and flowers being similar in form to Starina (Miniature — U.S. Plant Pat. No. 2,646 — expired).

The plant, which has a normal height of 16 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Four Seasons Rose Nursery, located at Bakersfield, Calif., under conditions of careful control and observation, as a cross between Rocky (floribunda — U.S. Plant Pat. No. 4,669) as the seed parent and an unnamed buff-yellow seedling (Matangi×Honey Hill) as the pollen parent.

Subsequent to origination of the variety I successfully reproduced it at my nursery, located as aforesaid, by budding as well as by cuttings; the reproductions have run true in all respects.

The color photograph illustrates the variety, including the foliage, buds, and flowers.

Referring now specifically to the new and distinct variety of rose plant, the following is a detailed description thereof in outline; all major color plate identifications being by reference to the British Colour Council Horticultural Colour Chart, except where common terms of color definition are employed.

Type: Hardy; dwarf; bushy; rounded; upright; seedling; greenhouse; outdoors; cut flowers; garden decoration.

Class: Miniature.

*International identification.*—variety: FOUtell.

*Commercial synonym.*—Show 'N' tell.

2

Flowers borne: Often singly but also in loose sprays of 3 to 5 or more on slender wirey stems.

Quantity of bloom: Abundant both outside and in greenhouse.

Bud:

*Peduncle.*—Average length; slender but sturdy; erect; medium green, sometimes lightly tinted bronze (outdoors).

*Hairs.*—Few or none.

*Before calyx breaks.*—Size—small.

*Form.*—Long; pointed with several small foliaceous apendages and several very small hairs on surface of bud; with foliaceous parts extending beyond the tip of the bud equal to one-half or more of its length.

Color: Medium green, occasionally tinted with bronze (outdoors).

*As calyx breaks.*—Color—orange-red to near-white.

*Opening.*—Opens well in all weather.

Bloom:

*Size when fully open.*—Small, averaging about 50 mm (2").

*Petalage.*—Double—averaging about 25–30 petals arranged regularly plus often several small petaloids.

*Form.*—High centered then becoming more rounded with petals reflexing loosely outward, and later at maturity, rolled loosely outward and downward. Open flowers may show stamens.

Petals: Fairly thick, velvety on inside and satiny on outside surface.

*Shape.*—Outside petals, borad lanceolate with acute tip; Intermediate — broad lanceolate with acute tip; Inside — lanceolate with rounded or notched tip.

Color: Newly opened flower from a plant grown in plastic greenhouse (March, 1989), Bakersfield, Calif.:

*Outside petal.*—Outside surface — ranging from near Mandarin Red 17/3 to white and blending into near Empire Yellow 603/2 on basal ¼ or less of petal (or basically white, the white being lightly tinted near Mandarin Red 17/3 from color bleeding through from the inner surface, giving the white a slightly pinkish tint which may vary in intensity depending on the time of year, light intensity, and other growing conditions). Outside surface of petal is sometimes slightly streaked, depending on the interaction of sunlight and opening sepals, the color of the streaking being near Mandarin Red 17/2 or similar. (NOTE: I find no comparable color in reference to the white flower color.) Inside surface — bright orange-red, near Mandarin Red 17, which is lightly veined or overlaid with darker or blackish-red, the exact veining or coloring being determined by the velvety texture of the petal surface which varies depending on the time of year, light intensity, and other growing conditions. The above color description (near Mardarin Red 17) blends into near Empire Yellow 603/2 on the basal ¼ or less of petal.

*Intermediate petal.*—Outside surface similar to outside petal. Inside surface — similar to outside petal.

*Inner petal.*—Outside surface — similar to intermediate petal. Inside surface — similar to intermediate petal. General color effect; newly opened flowers — bright orange-red. Three days open — color similar but less intense and yellow eye becoming white. Behavior — opens will in all weather. Spent petals drop off. Flower longevity (March 1989) — plant in pot — 4–5 days or longer. Cut flowers at living room temperature 4–5 days.

Reproductive organs:

*Stamens.*—Several, arranged regularly about pistils.

*Filaments.*—Varying length, medium long, yellow.

*Anthers.*—Yellowish.

*Pollen.*—Quite abundant.

*Pistils.*—Average number.

*Styles.*—Fairly even; short length; bunched; color — light yellow.

*Ovaries.*—All enclosed in calyx.

*Hips.*—Fairly plentiful, ball shaped, orange to russet.

*Sepals.*—Permanent; spear shape; recurved against peduncle.

*Seed.*—Several.

Foliage:

*Leaves.*—Compound of five (sometimes three or seven) leaflets; small to medium; leathery; semi-glossy.

*Leaflets.*—Shape: broad, lanceolate; apex acute; base rounded (sometimes acute). Margin serrate.

*Color.*—Ranging from near Parsley Green 00962 to near Parsley Green 00962/2 in the adult stage. Juvenile stage similar but often tinted red or bronze on new growth depending on time of year, light intensity, and other growing conditions.

*Rachis.*—Medium strength; upperside usually quite smooth, grooved; underside sparsley thorny (very small) with few or no tiny prickles.

*Stipules.*—Short to medium length; narrow to medium width; short length; narrow points which turn out usually at about 45 degrees.

Growth:

Habit.—Dwarf; bushy; rounded to upright; much branched.

*Growth.*—Free, vigorous; internodes short.

*Canes.*—Medium slender; sturdy.

*Main stems.*—Color: near Parsley Green 00962/2 or lighter. Newer growth similar in color, but often tinted red or bronze depending on time of year, light intensity, and other growing conditions.

*Thorns.*—Moderate amount. Prickles — moderate. Color: light brownish to gray on established growth; reddish to bronze on new growth.

*Branches.*—Color: near Parsley Green 00962/2 or similar. Thorns: moderate. Prickles: few to none. Hairs: none.

The miniature rose plant and its flowers as herein described may vary in slight detail due to climatic, soil, and cultural conditions under which the variety may be grown; the present description being of the variety as grown at Bakersfield, Calif.

The following is claimed:

1. A new and distinct variety of miniature rose plant of hardy, dwarf, bushy, rounded to upright, much branched habit, substantially as illustrated and described, characterized by buds and flowers of bright orange-red with lighter near-white reverse; the bud and flower resembling the variety Starina (U.S. Plant Pat. No. 2,646) in form; and further characterized by a plant of vigorous and compact growth habit, easy to propagate from cuttings or by budding, with an abundance of small to medium size semi-glossy foliage and an abundance of flowers borne both singly and in loose clusters of 3 to 5 or more.

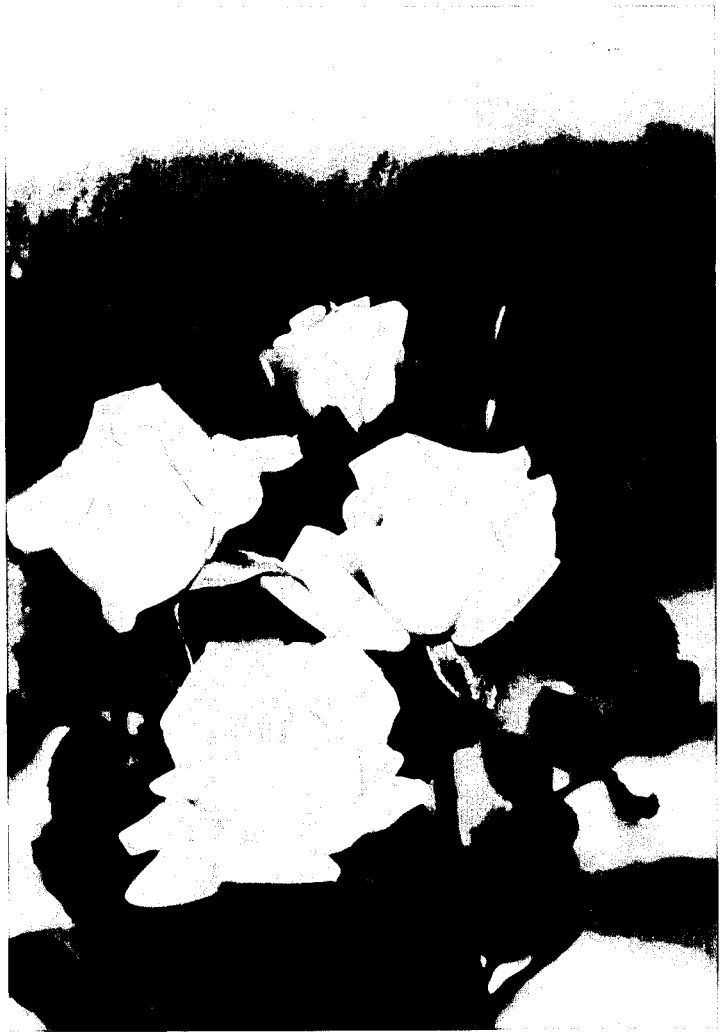

* * * * *